United States Patent
Sieller et al.

(10) Patent No.: US 7,156,819 B2
(45) Date of Patent: *Jan. 2, 2007

(54) FLEXION AND EXTENSION DEVICE

(75) Inventors: Richard T. Sieller, Virginia Beach, VA (US); Ronald B. Hopkins, Virginia Beach, VA (US)

(73) Assignee: R & R Holdings, LLC, Virginia Beach, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/987,739

(22) Filed: Nov. 12, 2004

(65) Prior Publication Data

US 2006/0106328 A1    May 18, 2006

(51) Int. Cl.
*A61F 5/00* (2006.01)
*A61F 13/00* (2006.01)

(52) U.S. Cl. .......................... 602/21; 602/64
(58) Field of Classification Search ............. 602/16, 602/20–22, 5, 60–64; 128/99.1, 101.1, 103.1, 128/108.1, 105.1; 482/44, 45, 46, 33; 601/40; 623/21.11

See application file for complete search history.

(56) References Cited

U.S. PATENT DOCUMENTS

| | | | |
|---|---|---|---|
| 494,197 A * | 3/1893 | Hall | 482/48 |
| 2,553,277 A | 5/1951 | Robinson et al. | |
| 2,767,708 A | 10/1956 | Keropian | |
| 3,707,963 A | 1/1973 | Keropain | |
| 4,100,918 A | 7/1978 | Glancy | |
| 4,191,373 A * | 3/1980 | Lancellotti | 602/16 |
| 4,291,421 A * | 9/1981 | Massey et al. | 623/63 |
| 4,677,971 A | 7/1987 | Lindemann | |
| 4,682,776 A | 7/1987 | Mitchell et al. | |
| 4,790,300 A | 12/1988 | Marx | |
| 4,862,878 A | 9/1989 | Davison et al. | |
| 4,949,711 A | 8/1990 | Gyovai et al. | |
| 5,002,044 A | 3/1991 | Carter | |
| 5,013,037 A | 5/1991 | Stermer | |
| 5,103,807 A * | 4/1992 | Makaran | 601/40 |
| 5,113,849 A | 5/1992 | Kuiken et al. | |
| 5,167,612 A * | 12/1992 | Bonutti | 602/20 |
| 5,213,094 A | 5/1993 | Bonutti | |
| 5,365,947 A | 11/1994 | Bonutti | |
| 5,383,845 A | 1/1995 | Nebolon | |
| 5,409,447 A | 4/1995 | Wedge, Jr. | |
| 5,456,268 A | 10/1995 | Bonutti | |
| 5,472,410 A | 12/1995 | Hamersly | |
| 5,527,040 A * | 6/1996 | Stanley et al. | 473/213 |
| 5,653,680 A | 8/1997 | Cruz | |
| 5,662,595 A | 9/1997 | Chesher et al. | |
| 5,683,353 A | 11/1997 | Hamersly | |

(Continued)

FOREIGN PATENT DOCUMENTS

EP    0 509 723    10/1992

(Continued)

*Primary Examiner*—Henry Bennett
*Assistant Examiner*—Shumaya Ali
(74) *Attorney, Agent, or Firm*—John H. Thomas, P.C.

(57) ABSTRACT

An orthotic device may be utilized to promote flexion or extension of a patient's wrist. At least one support member having a pivotal portion may be angularly positioned through the use of a tensioning member in conjunction with a hinge to effect the desired therapeutic fixation of the joint, or alternatively, to permit a limited range of motion. The tensioning member is connected on one end to a post, and on the other end to an anchor, wherein the positions of flexion or extension are created depending on the direction in which the tensioning member extends from the anchor to the post.

13 Claims, 3 Drawing Sheets

U.S. PATENT DOCUMENTS

| | | | |
|---|---|---|---|
| 5,685,830 A | 11/1997 | Bonutti | |
| 5,820,577 A * | 10/1998 | Taylor | 601/40 |
| 5,857,988 A | 1/1999 | Shirley | |
| 6,179,799 B1 * | 1/2001 | Doran | 602/20 |
| 6,371,932 B1 | 4/2002 | Foote | |
| 2002/0035342 A1 | 3/2002 | Williams | |
| 2003/0065281 A1 * | 4/2003 | Hopkins et al. | 602/5 |
| 2003/0073941 A1 | 4/2003 | Betz | |
| 2003/0144620 A1 * | 7/2003 | Sieller et al. | 602/5 |

FOREIGN PATENT DOCUMENTS

| | | |
|---|---|---|
| EP | 0 564 734 | 10/1993 |

* cited by examiner

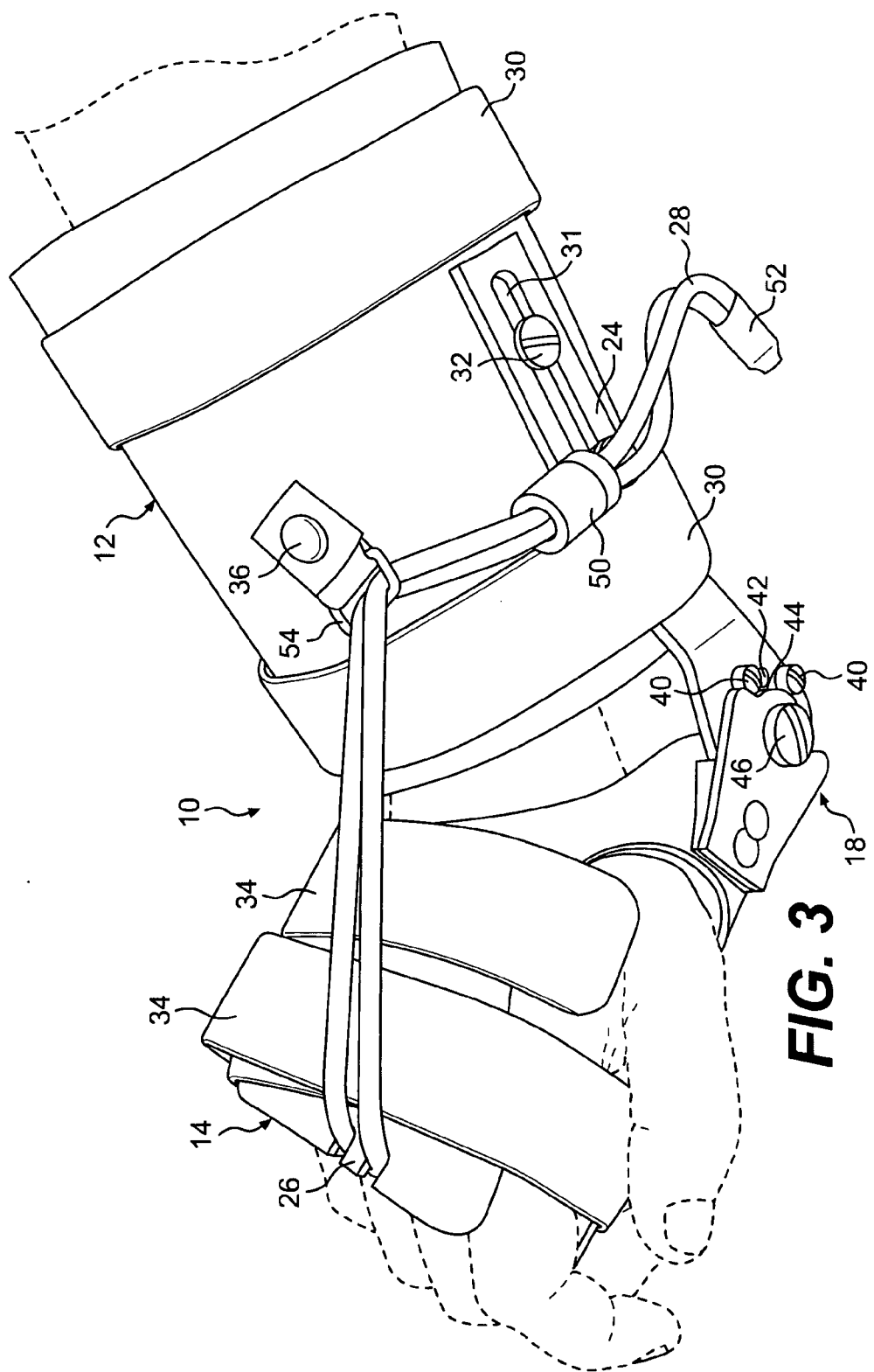

FLEXION AND EXTENSION DEVICE

FIELD OF THE INVENTION

The present invention relates to an orthotic device that promotes flexion and extension of a patient's wrist. An interaction of components promotes the rigid or controlled variable angular positioning of a patient's wrist to achieve therapeutic benefit. The force generated by the components and their direction can be quantified and used in therapeutic treatment.

BACKGROUND OF THE INVENTION

There are many known orthotic devices including those specifically directed to rehabilitation of various joints such as elbows, knees, wrists and ankles. Typically, these apparatuses are static or have a singular position achieved through the application of pressure and/or force that is applied during operation. Those forces may be uneven across the device. In some instances, an apparatus may have an adjustable force mechanism, but it ultimately operates within a limited range of positions. Usually, the forces are solely directed toward effecting a joint's extension or flexion, but not both.

A problem with prior art flexion or extension devices is their complex and bulky nature that may interfere with a patient's freedom of movement and comfort. Further, existing devices are often difficult to customize to meet the needs of a particular patient. Also, it may be cumbersome or impossible to modify the tension and/or angular positioning provided by existing devices as therapy progresses. Finally, the ability to provide either rigid or partially flexible support is not simultaneously achieved by conventional devices.

SUMMARY OF THE INVENTION

Accordingly, it is an object of the present invention to overcome the forgoing drawbacks and problems. The present invention provides a combination of components that promote flexion and extension of a wrist, which may be configured to produce static and/or variable directional forces. In addition, the present invention may provide optional contouring or padding to enhance comfort and/or rotational positioning, such as ulnar or radial deviation of a patient's wrist. Preferably, the forces generated by the present device can be quantified and used in therapeutic treatment in accordance with treatment guidelines.

In an embodiment, the orthotic device comprises a unitary support member having an integrated pivotal portion therein, wherein the support member is adapted to align to and support a patient's forearm and hand. The orthotic device may be comparable to a tight, semi-rigid sleeve made from an elastic material, or it may be fabricated primarily from a lightweight solid material such as plastic.

In an embodiment, the orthotic device comprises first and second support members that are connected at opposing ends, forming a pivotal portion. The first and second support members each have an inner surface for holding a patient's forearm and hand, and an outer surface facing the environment. The first support member is adapted to align against a forearm, and the second support member is adapted to support a hand. At least one post is disposed on the outer surface of the first support member, and at least one anchor is disposed on the outer surface of the second support member.

The device further comprises a tensioning member having a first end connected to an anchor and a second end connected to the post. At least one guide may be disposed on the outer surfaces of the first and second support members to direct the tensioning member toward a particular anchor. The tensioning member may be made of an elastic or inelastic material, and may have an adjustable length. The tensioning member assists in the flexion or extension of a wrist upon selection or positioning of appropriate guides and anchors disposed on the first and second support members, and the securing of an appropriate length of the tensioning member to a post and an anchor.

In an embodiment, the pivotal portion of the orthotic device may further comprise a hinge member. The hinge member may be used for maintaining a wrist in a fixed, predetermined angular position; alternatively, it may permit limited angular or rotational movement of the wrist. In an embodiment, the hinge member may operate to hold a fixed angle by twisting and locking at least one peg into a receptacle, thus securing the peg within one of an array of complimentary cavities strategically positioned to hold the orthotic device at selected angles for a patient's wrist. A locking pin within the hinge member may further assist in fixing a predetermined angle.

The orthotic device of the present invention may adjustably hold angles ranging from about +90° to about −90°, relative to the horizontal level of the forearm, and may also permit or restrict particular rotational movements. These positions may be achieved by the positioning of the hinge member, the tensioning member, or through complementary interactions attributed to both the hinge member and tensioning member. In addition, the operation of the hinge member and tensioning member may independently or cooperatively contribute to a wrist's limited range of movement, specifically, to permit limited movement but only within a prescribed angular or rotational range. Further, a wrist may be held in a position in which movement in one direction is prevented, but some movement in an opposing direction is permitted.

In another embodiment, an orthotic device for promoting flexion and extension includes a first support member for aligning against a forearm and a second support member for supporting a hand. The first support member may be adapted to wrap around a forearm, and may further comprise at least one strap for securing the first support member to a forearm. The second support member may be adapted to permit free movement the forefingers and thumb, wherein at least one band may secure the second support member to the dorsal and palmar surfaces. Additional contouring of the first and second support members may be achieved through specific molding of the orthotic device during its formation, or through the use of inserted padding, where particular rotational positioning of a wrist may be desired.

In an additional embodiment, a kit is disclosed for use in assembling an orthotic device that includes a first support member adapted to align against a forearm, and a second support member adapted to support a hand. The kit also includes a post mountable on the first support member, and an anchor mountable on the second support member. The kit further includes a tensioning member connectable on one end to the anchor and on the other end to the post.

BRIEF DESCRIPTION OF THE DRAWINGS

FIG. 3 is a perspective view of one embodiment of an orthotic device in accordance with the present invention, with the device shown in an extended position.

DETAILED DESCRIPTION OF THE PREFERRED EMBODIMENTS

The present invention is directed to an orthotic device used to promote flexion and/or extension of a patient's wrist. Positioning of the wrist in which the wrist is bent such that palm of the hand is facing downward, or passively conforming to gravity when arms are extended, is called flexion. Positioning in which the wrist is bent such that the palm of the hand is pulled upward or skyward, against the force of gravity when arms are extended, is called extension. The orthotic device described herein can apply either dynamic or static forces to fix or limit a wrist's flexion or extension, and may also provide positioning or support that constrains ulnar or radial deviation of a wrist. Further, both the positioning as well as degree of movement permitted by the device may be adjusted by a user or therapist in accordance with the needs or therapeutic plan for a patient.

Figure 1:
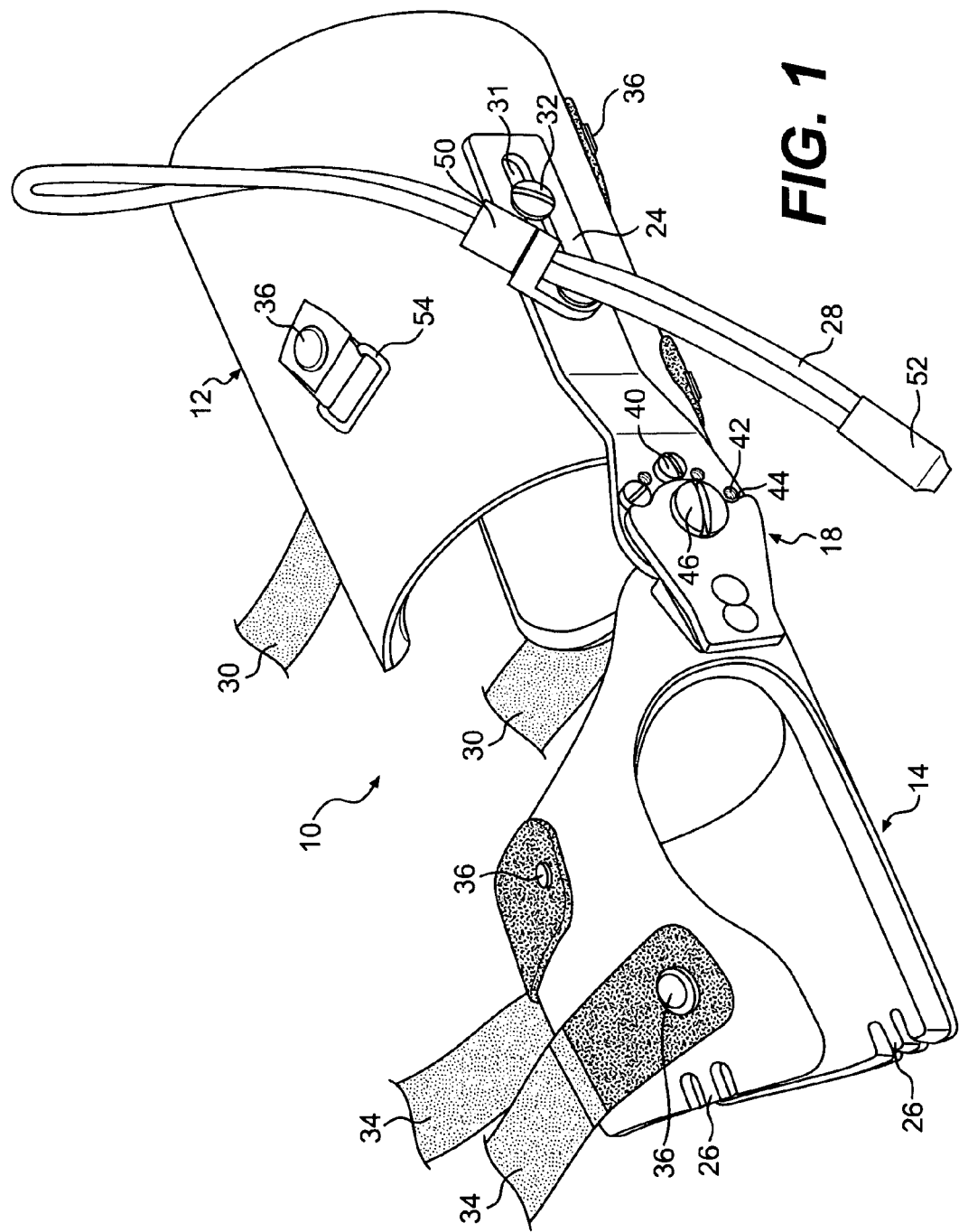
FIG. 1 is a perspective view of one embodiment of an orthotic device in accordance with the present invention.
Figure 2:
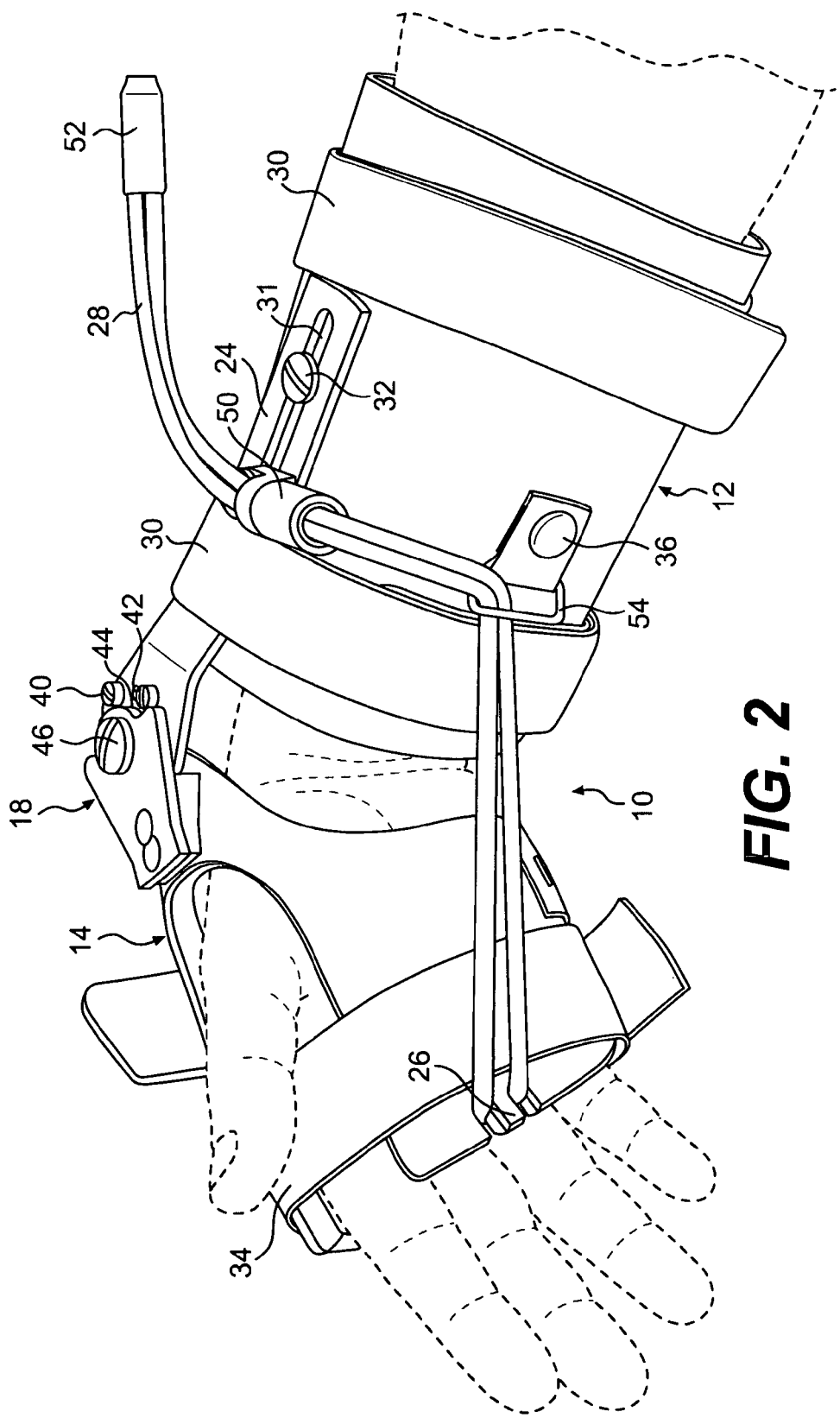
FIG. 2 is a perspective view of one embodiment of an orthotic device in accordance with the present invention, with the device shown in a flexed position.

Referring to the drawings, FIGS. 1, 2, and 3 illustrate an orthotic device in accordance with an example of the present invention. The teachings of the embodiments described herein may be applied to other devices for joint therapy in accordance with the present disclosure.

The orthotic device 10 is a brace adapted to support a patient's lower forearm, wrist, and hand. The device 10 includes a first support member 12 and second support member 14 that are connected at adjacent ends by a hinge 18. The first support member 12 is adapted to align against a forearm, and the second support member 14 is adapted to support a hand.

A post 24 is disposed on the first support member 12, and at least one anchor 26 is disposed on the second support member 14. The post 24 may be adapted to permit slidable positioning of a tensioning member 28 through the use of a knob 32 disposed within a groove 31. A post 24 may be made from any material that is suitable to fix a tensioning member 28 in place, such as a screw, knob, a slot with a locking cover, or any combination thereof. An anchor 26 may be fashioned from a pair of notches (shown), a knob, a suction cup with a projection, an opening or plurality of openings, a clamp, or any other article useful for holding the tensioning member 28 in position on the second support member 14.

Alternatively, an anchor 26 may be moveable, such as a locking knob within a slot, so that its position may be adjustable. An anchor 26 may be positioned on either or both the first 12 or second 14 support members, depending on the location of the post 24 which may be placed in any strategic location to effect a therapeutic benefit. As shown in FIG. 1, the tensioning member 28 may direct flexion or extension moments through fixation on the alternative anchors 26 generally located centrally on the dorsal and palmar regions of the second support member 14. In addition, the promotion or restriction of ulnar or radial deviation may also be achieved through the positioning of anchors 26 at more lateral locations on the second support member 14.

The first support member 12 may be configured to substantially circumscribe a forearm, and may optionally employ straps 30 to better align the first support member 12 against a forearm. The second support member 14 may be adapted provide support to the dorsal and palmar surfaces of a hand while permitting environmental interactions by the fingers and thumb, and may optionally employ bands 34 for securing the second support member 14 to a hand. The straps 30 and bands 34 may be attached to the first 12 and second 14 support members by attachment screws 36, and fashioned from hook and loop fasteners (such as VELCRO), which may be adjustable in length to conform to a particular patient's size and comfort level.

The first 12 and second 14 support members are preferably made from a generally stiff material. For instance, if the enclosure is a cast, acceptable cast materials include Kydex. However, the material of the first 12 and second 14 support members may also be a tight elastic sleeve-type substance that provides both support to the limbs as well as a surface allowing pivotal positioning of the joint and the mounting of a tensioning member 28 to the device 10. In general however, the first 12 and second 14 support members may be fabricated from any suitable material that meets the functional requirements described herein, and a plastic material is preferred for its light weight and inexpensive cost.

The hinge 18 connects the lower end of the first support member 12 to the upper end of the second support member 14. The hinge 18 may be positioned to hold a particular flexed or extended position through the twisting and locking at least one peg 40 releasably placed into a receptacle 42, thus securing the peg within one of an array of complimentary cavities 44 strategically arranged to hold the orthotic device at a variable selected angle. The fixation of angular positioning of the hinge 18 may be further secured by a locking pin 46. The pegs 40, cavities 44, and locking pin 46 may be fabricated from any solid substance that could sustain substantial force, preferably metallic substances, but could potentially include plastic or other synthetic materials.

In utilizing the hinge 18 to provide angular positioning of a wrist, a therapist or patient could determine a desirable angle or range of motion for a patient, or the device could be preset and locked at a single angle that would be unmovable and nonadjustable. For instance, as shown in FIGS. 1–3, the selection of pegs 40 in particular cavities 44 could permit movement in a limited range, provided that the locking pin 46 were not completely tightened to restrict movement. The hinge 18 could also be a universal or ball-and-socket type element that permits rotational or pivotal movement in multiple planes. Thus, a hinge 18 would be designed to permit and/or restrict the desired movement of a wrist, including flexion, extension, ulnar or radial deviation, and combinations thereof.

In an embodiment, the first 12 and second 14 support members could be custom-molded with contours, or supplied with conventional contouring or padding, to conform a patient's hand to a rotational angle that either enhances or restricts ulnar or radial deviation of a patient's wrist.

The tensioning member 28 may be made from any substance, including an elastic, plastic, or metal cord or spring, or any other rigid or semi-rigid article for connection. As shown in the drawings, the tensioning member 28 is a rubber or bungee-type continuous loop. The tensioning member may be secured to the post 24 by a grip-type clamp 50 that is adjustable for securing a particular length of loop extending from the post 24 to fasten to an anchor 26. A cap 52 may be used to hold the ends of the tensioning member 28 and provide closure to its loop.

At least one guide 54 may be secured to first 12 and/or second 14 support members of the device 10 by an attaching screw 36, wherein a guide 54 is used to direct the tensioning member to an appropriate anchor 26. A guide 54 may be configured to receive the tensioning member 28 through a ring-shape aperture, which after passing through it, the tensioning member 28 secures to an appropriate anchor 26 to facilitate flexion or extension of a patient's wrist.

As shown in FIGS. 1 and 2, a guide 54 is selected on the ventral region of the first support member 12 in proximity to the juncture of the patient's wrist and palm of the hand. When the tensioning member 28 is run through this guide 54 and secured to an anchor 26 on the palmar region of the second support member 14, flexion of a patient's wrist is achieved. In contrast, as shown in FIG. 3, when the tensioning member 28 is run through a guide 54 on the dorsal region of the first support member 12 and secured to an anchor 26 located in proximity to the outer knuckle region of the fingers, extension of a patient's wrist is achieved. Thus, selection of an appropriate guide 54 and anchor 26 enable a tensioning member 28 of a preselected length and flexibility to contribute to the angular positioning achieved by the hinge 18. It is also contemplated that a plurality of tensioning member and anchor combinations could be utilized to achieve more complex therapeutic goals in one orthotic device.

In operation, a patient's hand and forearm are placed in the first 12 and second 14 support members, and secured by straps 30 and bands 34. The tensioning member 28 is mounted on a post 24 that may be disposed on the first support member 12, and set to a predetermined length by the clamp 50. The tensioning member 28 may then be directed through an appropriate guide 54 and secured to an anchor 26 that may be on the second support member 14. The hinge 18 may be permitted limited movement due to the degree of elasticity of the tensioning member 28. Alternatively, the hinge 18 may fix the angular positioning of a wrist by locking into place at least one peg 40 in a receptacle 42, thereby holding the peg 40 in a selected cavity 44 that sets an angular position. The fixed angle may be further secured by the tightening of a locking pin 46 that holds the hinge in position.

In addition, at least one post 24, guide 54, and anchor 26 could be located anywhere on the first 12 or second 14 support members to permit a therapist to choose from several alternatives on a single device for positioning a patient's wrist. The tensioning member 28 may be directed from any location on the device 10 to an anchor on the same or opposite side of the device 10.

In modifying the position or configuration of the device 10, removable attachment screws 36 may be used for holding the guides 54, straps 30, and bands 34, and to reposition elements on the first 12 and second 14 support members as needed. Also, it may be necessary to remove the straps 30 and bands 34 to wash or replace them for sanitary reasons. It is further contemplated that padding or contouring may be incorporated in the first 12 and second 14 support members to enhance comfort and facilitate positioning, and also that the straps 30 and bands 34 may be made from any elastic or inelastic material to enhance comfort and therapeutic benefit.

In addition to the beneficial and qualitative uses already described herein, a device may also have quantitative features incorporated into it. For instance, a hinge having a spring mechanism or some other dynamic mechanism that provides a measurable, and preferably adjustable, rotational force in either direction of flexion or extension or other direction. Similarly, a tensioning member may include a component for measuring the amount of force being exerted by the tensioning member. In any case, the quantification of treatment may be used in therapy to identify specific progress of the therapy.

The device described herein is intended to be simple to use and available to any patient or therapist. Therefore, it is envisioned that a kit containing the unconnected components described herein will be available to users or to therapists. Since some of the components may vary in size or length, depending on the needs of a given patient, it will be possible to select among possible parts included in the kit to meet individual requirements.

While the invention has been described with reference to specific embodiments herein, it will be understood that numerous variations, modifications and additional embodiments are possible, and accordingly, all such variations, modifications, and embodiments are to be regarded as falling within the spirit and scope of the present invention.

What is claimed is:

1. An orthotic device for promoting flexion and extension comprising:
   a first support member adapted to support a distal portion of an arm;
   a second support member adapted to support a hand, wherein the second support member is connected to the first support member;
   a hinge portion for connecting the first support member to the second support member;
   at least one post mounted on the first support member;
   a pair of anchors mounted on opposing sides of the second support member; and
   a tensioning member connected on one end to an anchor and on the other end to a post, wherein the anatomical force of flexion or extension of a wrist is created depending on the location of the anchor the tensioning member is connected to when extended from a post.

2. An orthotic device as claimed in claim 1, further comprising at least one guide for directing the tensioning member from an anchor to a post.

3. An orthotic device as claimed in claim 1, further comprising at least one strap for securing the first support member to a forearm.

4. An orthotic device as claimed in claim 1, further comprising at least one band for securing the second support member to a hand.

5. An orthotic device as claimed in claim 1, wherein at least one anchor may be movable and securable to the second support member to achieve a particular position and force on a wrist when connected to the tensioning member.

6. An orthotic device as claimed in claim 1, wherein the tensioning member has an adjustable length.

7. An orthotic device as claimed in claim 1, further comprising a clamp for adjusting and holding the tensioning member at a fixed length.

8. An orthotic device as claimed in claim 1, wherein the tensioning member is comprised of an elastic material.

9. An orthotic device as claimed in claim 1, wherein the tensioning member is comprised of an inelastic material.

10. An orthotic device as claimed in claim 1, wherein the first support member is fixedly connected to the second support member at a predetermined angle at the binge portion.

11. An orthotic device as claimed in claim 1, wherein the first support member is movably connected to the second support member at the hinge portion.

12. An orthotic device as claimed in claim 11, wherein the first support member is movably connected to the second support member to set a predetermined angular and planar range of motion.

13. An orthotic device as claimed in claim 1, wherein the hinge portion further comprises quantitative means for exerting a rotational force on the device.

* * * * *